(12) United States Patent
Ratner

(10) Patent No.: US 8,893,716 B2
(45) Date of Patent: Nov. 25, 2014

(54) DISPOSABLE BREATHING ASSISTANCE DEVICE WITH MANOMETER

(75) Inventor: Jeffrey Bruce Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 1256 days.

(21) Appl. No.: 12/589,219

(22) Filed: Oct. 20, 2009

(65) Prior Publication Data

US 2011/0088696 A1 Apr. 21, 2011

(51) Int. Cl.
*A61M 16/00* (2006.01)
*A62B 7/00* (2006.01)
*A61M 16/20* (2006.01)
*A61M 16/08* (2006.01)

(52) U.S. Cl.
CPC ......... *A61M 16/208* (2013.01); *A61M 16/0816* (2013.01); *A61M 16/0858* (2013.01); *A61M 16/209* (2013.01); *A61M 2016/0027* (2013.01)
USPC ............ 128/204.18; 128/205.24; 128/204.22; 128/204.23; 128/204.24; 128/207.14

(58) Field of Classification Search
USPC ............ 128/205.24, 204.18, 204.22–204.24, 128/200.24, 203.12, 203.15, 203.14, 128/207.14–207.18
See application file for complete search history.

(56) References Cited

U.S. PATENT DOCUMENTS

| | | | |
|---|---|---|---|
| 5,036,847 A | 8/1991 | Boussignac | |
| 5,193,532 A | 3/1993 | Moa | |
| 5,538,002 A | 7/1996 | Boussignac | |
| 6,009,869 A * | 1/2000 | Corbeil | 128/200.21 |
| 6,273,087 B1 | 8/2001 | Boussignac | |
| 6,363,935 B1 | 4/2002 | Boussignac | |
| 6,516,801 B2 | 2/2003 | Boussignac | |
| 6,761,172 B2 | 7/2004 | Boussignac | |
| 6,814,075 B2 | 11/2004 | Boussignac | |
| 7,051,596 B1 | 5/2006 | Lau | |
| 7,331,344 B2 | 2/2008 | Foster | |
| 7,357,033 B2 | 4/2008 | Lau | |
| 2008/0283062 A1* | 11/2008 | Esposito, Jr. | 128/204.23 |
| 2009/0044807 A1 | 2/2009 | Boussignac | |

* cited by examiner

*Primary Examiner* — Justine Yu
*Assistant Examiner* — Colin W Stuart
(74) *Attorney, Agent, or Firm* — Larson & Larson, P.A.; Frank Liebenow; Justin P. Miller

(57) ABSTRACT

A disposable breathing assistance device with manometer for monitoring the pressure within the device is capable of providing CPAP and in some embodiments includes a deflection face to prevent injected jets of supplementary respirable gas from directly striking the patient's mucosa. The breathing assistance device further optionally includes a safety pressure relief valve as an additional safety against overpressure within the device. A specialized supplementary respirable gas inlet provides improved pressure characteristics.

15 Claims, 8 Drawing Sheets

US 8,893,716 B2

DISPOSABLE BREATHING ASSISTANCE DEVICE WITH MANOMETER

BACKGROUND OF THE INVENTION (1) Field of Invention

The present invention relates to the field of breathing assistance devices.

(2) Description of Prior Art

Breathing aids or breathing assistance devices are well known in the art. Numerous devices have been disclosed which are designed to assist a patient who is having difficulty breathing. These devices often supply supplemental oxygen at a concentration higher than that in the atmosphere, and often under pressure, as a means of promoting improved respiration and/or improved oxygen absorption. Further, numerous breathing assistance devices which are designed to provide a continuous positive airway pressure (CPAP) have likewise been disclosed.

For example, U.S. Pat. No. 5,036,847, by Boussignac et al., discloses a breathing aid comprising a tubular main channel through which respiration occurs, with one end (proximal end) open to the atmosphere and at least one additional auxiliary channel opening into the main channel through which supplemental pressurized respirable gas (e.g. oxygen) is provided to the patient. The device produces a continuous positive airway pressure (CPAP). The invention of U.S. Pat. No. 5,036,847 also comprises a deflection face as a means to deflect the jet(s) of respirable gas exiting the auxiliary channel(s) towards the center of the main channel so that the jet(s) of respirable gas does not directly strike the patient's mucous membranes. Further, the disclosure also provides for an additional channel which opens into the distal end face (user end) of the tube and which may be connected to a pressure measurement device as well as a safety pressure relief device (perforations through the main tube in conjunction with a safety sleeve) to relieve pressure within the main tube in the event that the internal pressure becomes too high.

U.S. Pat. No. 5,538,002, U.S. Pat. No. 6,273,087, U.S. Pat. No. 6,363,935, U.S. Pat. No. 6,516,801, U.S. Pat. No. 6,761,172, and U.S. Pat. No. 6,814,075, as well as U.S. patent application Ser. No. 12/282,044, all by Boussignac (et al.), each likewise disclose similar inventions with various additional features. Many of these provide for a calibrated pressure relief valve in the proximal region of the main tube to relieve pressure in the main channel in the case of overpressure. Most of these require that the auxiliary channel(s) open into the main tube near ("close to," "in proximity of," "in the vicinity of") the distal end of the device.

As another example, U.S. Pat. No. 5,193,532 by Moa et al., discloses a breathing assistance device which produces a continuous positive airway pressure by means of an ejector action due to the influx of supplemental respirable gas into a breathing channel through an inlet channel. This device, like the Boussignac devices referred to above, also exhibits a branch channel open to the atmosphere and is therefore not a closed circuit, ventilator type CPAP system. Further, in this device the breathing channel (first branch channel) and the exhaust channel (second branch channel) are not linearly aligned but rather form an angle of 30 to 50 degrees with one another.

U.S. Pat. No. 7,331,344, by Foster et al., discloses yet another example of a "breathing device" wherein supplemental respirable gas is provided into a breathing channel through an inlet channel. As in the above examples, the exhaust channel in this invention is open to the atmosphere. And here, once again, the breathing channel and exhaust channel are not collinear but rather form an oblique angle with one another. The inlet channel is laterally offset from the breathing channel so as to introduce supplemental respirable gas in such a manner that a "bypass" occurs, whereby some portion of the supplemental respirable gas goes directly to the exhaust channel. According to the author, "It has been recognized that the phenomena of jet bypass, whereby a proportion of the fresh gas supplied to the patient passes directly out of the exhaust tube is crucial in giving the low added work of breathing." Col. 1, Lines 38-41.

Each of the above-described devices provide an exhaust channel open to the atmosphere yet provide a continuous positive airway pressure at the user end of the device. The use of continuous positive airway pressure both forces gas into the lungs during inhalation and forces the patient to exhale against pressurized gas during exhalation which may prevent the alveoli from collapsing. It has been found that in many cases, the use of such a CPAP device is of great assistance to patients experiencing breathing difficulties.

SUMMARY OF THE INVENTION

The applicant has discovered numerous disadvantages to previously disclosed inventions. Where one desires to ascertain and control the pressure within any of the aforementioned prior art devices for safety purposes or for the purpose of more precisely controlling the internal pressure in the device, etc., an external manometer must be attached to the device. Many prior art devices do not readily permit attachment of a manometer for internal pressure measurement and thus internal pressure measurement becomes difficult or impossible. Those prior art devices which exhibit an arrangement which accommodates attachment of an external manometer have multiple disadvantages including:

1) requiring the implementer to stock multiple parts in addition to the breathing assistance device, such as manometers, connecting tubes, etc. and have them available and ready for use when the need arises;
2) requiring sterilization of repeat use manometers after previous use;
3) exhibiting additional openings/ports through which air can escape resulting in a situation where it is potentially more difficult to control pressure within the device and/or where internal pressure is more likely to change when new devices are connected to the breathing assistance device;
4) exhibiting additional attachment openings/ports which can be confused with one another when attaching external equipment resulting in an increased likelihood of potentially incorrect and dangerous equipment setup;
5) lacking the guaranteed built-in safety feature of pressure indication thereby increasing likelihood of dangerous error and potential lawsuit;
6) increasing likelihood that a manometer might not be used in conjunction with the device resulting in greater difficulty in precisely controlling internal pressure as well as failure to make valuable information available which could make a difference in patient treatment;
7) requiring greater setup time as more time is required to connect an external manometer;
8) risking the possibility of incompatibility between different size connecting tubes, ports, etc. resulting in inability to successfully attach a manometer to the breathing assistance device;
9) creating a configuration involving tubes, connecters, etc. where an attached manometer may ultimately not be appropriately positioned for easily accessible observation of the pressure indication;

Applicant solves these problems by incorporating a disposable manometer into a completely disposable breathing assistance device.

Thus, the present invention yields a completely disposable breathing assistance device with built-in pressure measurement and readily perceived indication of current internal pressure. Various embodiments and/or applications of the device are capable of providing continuous positive airway pressure (CPAP) to the user. Further, the present invention may optionally include a calibrated pressure relief valve for added safety. Additionally, a specialized supplementary respirable gas inlet design which yields improved pressure characteristics and increased efficiency of supplementary respirable gas usage is disclosed.

REFERENCE NUMERALS IN DRAWINGS

Figure 1:
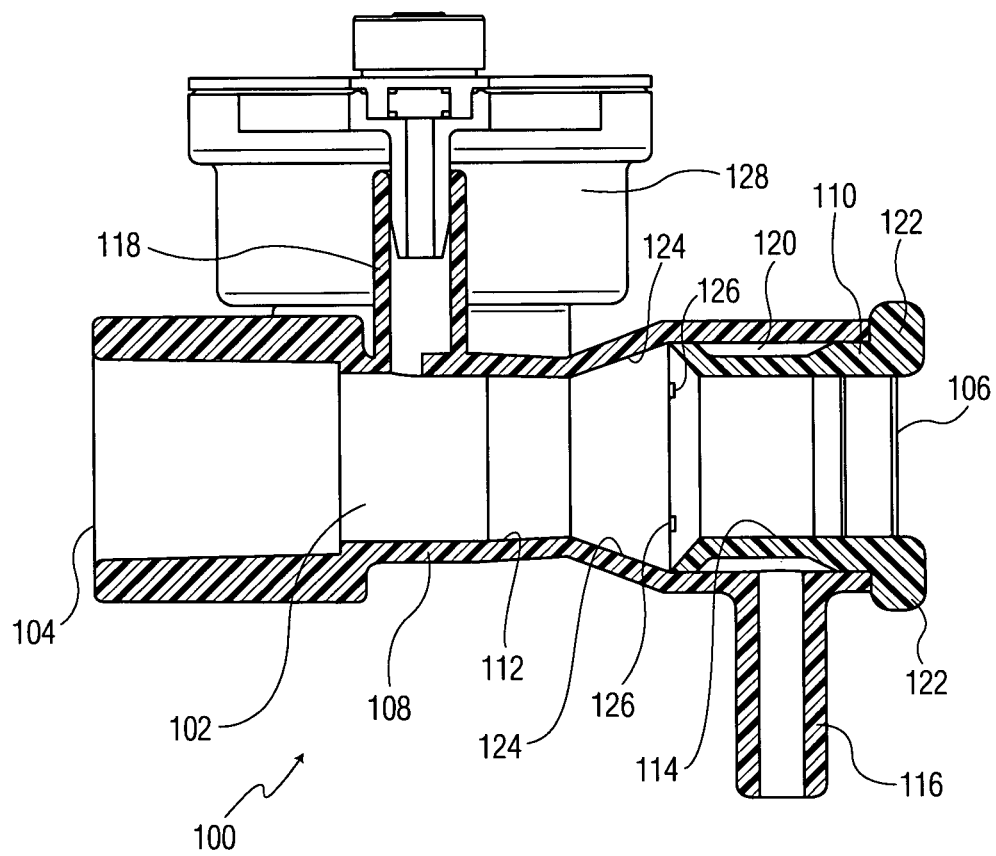
FIG. 1 shows a sectional view of an example of a breathing assistance device according to the present invention.

100 An example of a breathing assistance device
102 Main tube
104 Distal end of main tube
106 Proximal end of main tube
108 Main tube outer shell
110 Distribution ring/safety fin insert piece
112 Interior surface of the main tube outer shell
114 Inner surface of the distribution ring
116 Side port
118 Manometer port
120 Distribution ring
122 Safety fin
124 Deflection wall inside main tube
126 Supplementary respirable gas inlet
128 Manometer
302 Outer surface of the distribution ring/safety fin insert piece
304 Distribution ring cavity
306 Distribution ring outlet notches
400 An example of a breathing assistance device with pop-off safety relief valve
402 An example of a pop-off safety relief valve
404 Pressure relief throughhole through distribution ring/safety fin insert piece
406 Distribution ring/safety fin insert piece for a breathing assistance device with pop-off safety relief valve
408 Pressure relief throughhole through main tube outer shell
410 Main tube outer shell
412 Housing of ball and spring pop-off safety pressure relief valve
414 End cap of ball and spring pop-off safety pressure relief valve
416 Ball of ball and spring pop-off safety pressure relief valve
418 Spring of ball and spring pop-off safety pressure relief valve
420 Main tube
422 Pressure relief vent
424 Proximal end of the main tube
426 Safety fin
428 Interior surface of the main tube outer shell
430 Supplementary respirable gas inlet
432 Side Port
434 Distal end of main tube
436 Distribution ring
438 Manometer port
502 Distribution ring outlet notches
602 Specialized supplementary respirable gas inlet
604 Distribution ring/safety fin insert piece for example with specialized supplementary respirable gas inlet
606 Distribution ring
702 Distribution ring opening of the specialized supplementary respirable gas inlet
704 Rounded lengthwise edges of the specialized supplementary respirable gas inlet
706 Opening into main channel of the specialized supplementary respirable gas inlet
708 Straight lengthwise edges of the specialized supplementary respirable gas inlet
710 Distribution ring outlet notches on distribution ring/safety fin insert piece for example with specialized supplementary respirable gas inlet

DETAILED DESCRIPTION OF THE INVENTION

General Description

The present invention is a breathing assistance device. The invention comprises a main conduit having a proximal end, through which the main conduit is in fluid communication with the atmosphere, and an open distal end which is engageable with the breathing tract of a user. The distal end of the device may either be designed to be engaged directly with the breathing tract of the user or designed to be engaged indirectly (e.g. via a connector, mask, endotracheal tube, tracheostomy tube, etc.) with the breathing tract of the user. The device further comprises a means to connect to a source of supplementary respirable gas such that supplementary respirable gas, such as concentrated oxygen, may be injected via one or more supplementary respirable gas inlets into the interior of the main conduit and then inhaled by the user along with the atmospheric air which enters the main conduit via the proximal end of the main conduit. Preferably the injected flow(s) or jet(s) of supplementary respirable gas entering the main conduit via the supplementary respirable gas inlet(s) are directed substantially towards the cross-sectional center (i.e. lengthwise axis) of the conduit so as to avoid directly striking the mucosa of the user. Upon exhalation, the exhaled gas exits through the main conduit out the proximal end of the device into the atmosphere.

The invention further comprises a manometer engaged with the interior of the main conduit so as to measure the pressure within the main conduit and preferably continuously provides a conveniently discernable current indication of this pressure. In addition, the invention may further comprise a safety pressure relief valve designed to relieve pressure from the interior of the main conduit should the pressure within the main conduit become excessive. A specialized supplementary respirable gas inlet design is disclosed which yields improved pressure characteristics at the distal (patient) end of the device, thereby reducing the amount of supplementary respirable gas needed to achieve a given pressure at the distal end of the device.

Specific Embodiments of the Invention

Figure 2:
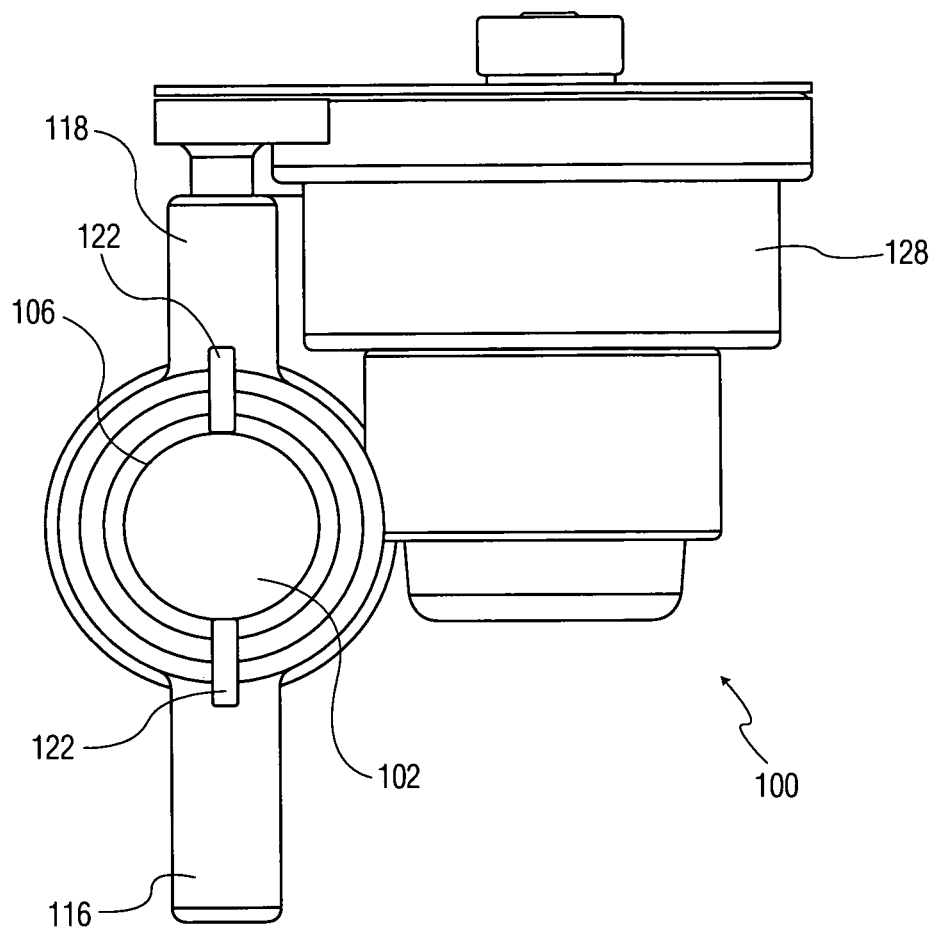
FIG. 2 shows the proximal end view of an example of a breathing assistance device according to the present invention.
Figure 3:
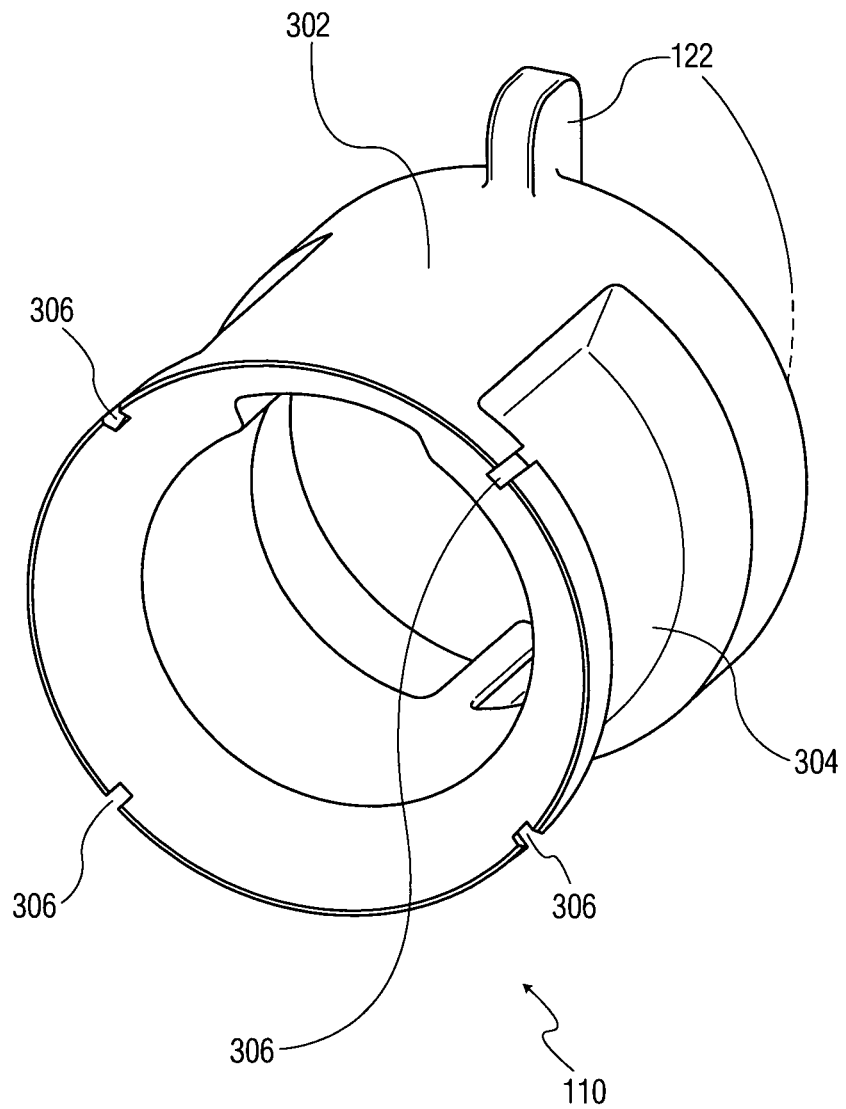
FIG. 3 shows an oblique angle view of an example of a distribution ring/safety fin insert piece according to the present invention.

Referring to FIGS. 1, 2 and 3, one embodiment (100) of the present invention comprises a linear substantially tube-shaped conduit, the main tube (102), having an open distal end (104) and an open proximal end (106). The main tube (102) comprises 2 attached pieces in this illustrated example, the main tube outer shell (108) and the distribution ring/safety fin insert piece (110). Together, the interior surface (112) of the main tube outer shell (108) and the inner surface (114) of the distribution ring/safety fin insert piece (110) boundary the interior space of the main tube (102). The proximal end of the main tube (106) is left open to the atmosphere such that gas may flow freely in and out of this open end. The open distal end (104) of the main tube (102) in this example is designed to be engaged indirectly with the breathing tract of a patient. The open distal end (104) of the device in this example is designed to receive a standard mask or endotracheal tube connector and may therefore be engaged via such a standard connector (not shown) with the external end of an endotracheal tube, a tracheostomy tube, mouthpiece, or the like, so that the device may be incorporated into the breathing path of a patient. (In general though, the invention may be practiced in such a way as to allow for either direct or indirect engagement with the breathing tract of a patient depending upon preference.)

The main tube outer shell (108) further comprises a side port (116) and a manometer port (118). The side port (116) of this embodiment is designed to be engaged via a standard connecting tube (not shown) with a source of supplementary respirable gas (not shown). The disposable manometer (128) is engaged into the manometer port (118). The sensing port of the disposable manometer (128) may be press fit, glued or otherwise firmly seated into the manometer port (118).

The distribution ring/safety fin insert piece (110) is mounted inside the proximal end region of the main tube outer shell (108) such that the inner surface (114) of the distribution ring/safety fin insert piece (110) forms a substantially contiguous surface with the interior surface (112) of the main tube outer shell (108) and such that a distribution ring (120), a substantially annular space, is formed between the interior surface (112) of the main tube outer shell (108) and the outer surface (302) of the distribution ring/safety fin insert piece (110). The distribution ring (120) is boundaried by the distribution ring cavity (304) and the interior surface (112) of the main tube outer shell (108) in this region. In the illustrated example, the distribution ring (120) does not extend the full 360 degrees around the circumference of the main tube (102) and thus is not a complete "ring" but this is simply a design choice and the distribution ring could likewise be designed to extend fully around the circumference of the tube.

This embodiment of the invention also comprises safety fins (122) which are an integral part of the distribution ring/safety fin insert piece (110). The distribution ring/safety fin insert piece (110) is positioned such that the safety fins (122) extend outward and radially from the proximal end (106) of the main tube (102). This configuration presents an uneven end surface with protrusions to decrease the likelihood of an object inadvertently obstructing the proximal end (106) of the main tube. Thus a solid foreign object is less likely to be able to snugly cover and/or obstruct the proximal end of the main tube (106) and cause an impedance or stoppage of the gas flow through the main tube (102).

In this example, the interior surface (112, 114) of the main tube (102) narrows, beginning at the distal end of the distribution ring/safety fin insert piece (110), along the distally following section of main tube (102) length. This narrowing configuration creates a deflection wall (124) on the interior surface (112) of the main tube outer shell (108) angled towards the cross-sectional center (i.e. lengthwise axis) of the interior of the main tube (102).

The side port (116) is in fluid communication with the distribution ring (120), which is likewise in fluid communication with the interior of the main tube (102) via supplementary respirable gas inlets (126). In this example, these supplementary respirable gas inlets (126) serve as, and may alternatively be viewed as, distribution ring outlets into the interior of the main tube (102). The 4 supplementary respirable gas inlets (126) in this example are formed between the inner surface (112) of the main tube outer shell (108) and the distribution ring outlet notches (306) which are small substantially rectangular indentations in the distal end edge of the distribution ring/safety fin insert piece (110).

In use, supplementary respirable gas flows from a supplementary respirable gas source, such as an oxygen tank or the like, into the side port (116) and then into the distribution ring (120). The supplementary respirable gas then enters into the interior of the main tube (102) from the distribution ring (120) through the 4 supplementary respirable gas inlets (126). These 4 flows of supplementary respirable gas into the interior of the main tube (102) are directed towards the cross-sectional center of the interior of the main tube by the deflection wall (124). Under sufficient pressure from the supplementary respirable gas source these flows of supplementary respirable gas are jets which are directed by the deflecting wall (124) towards the cross-sectional center of the interior of the main tube (102), converging upon one another and creating a positive pressure within the interior of the main tube (102).

In this way, the pressurized jets of supplementary respirable gas exiting from the distribution ring (110) and entering the interior of the main tube (102) through the supplementary respirable gas inlets (126) do not directly strike the mucosa of the patient but rather impinge upon one another in the center of the main tube (102), translating their kinetic energy into pressure within the main tube (102). The pressure within the main tube (102) at any given moment will be dependent upon the pressure of the jets of respirable gas entering the main tube (102) via the supplementary respirable gas inlets (126) as well as upon the transient flows of gas due to the patient's inhalation and exhalation through the main tube (102) during respiration. With an appropriate pressure from the supplementary respirable gas source, a CPAP (continuous positive airway pressure) is produced for the patient. At lower pressures from the supplementary respirable gas source, a more passive supplementation of respirable gas may be provided to the patient.

The manometer (128), which is in fluid communication with the interior of the main tube (102) via the manometer port (118), provides indication of the gas pressure within the interior of the main tube (102) on a continuous and immediate basis. In this example, the manometer port (118) is located approximately one third of the length of the main tube (102) from the distal end of the device (104) and so provides continuous indication of the pressure at this point in the interior of the main tube (102), in the region near where the jets of supplementary respirable gas entering the main tube (102) from the supplementary respirable gas inlets (126) converge. The currently described and illustrated configuration provides a readily discernible display directly on the side of the device of the pressure in this region inside the main tube (102). Such a prominent and easily perceived indication of internal pressure provides both convenience for one monitoring and/or applying the device as well as added safety for the patient.

As an example of appropriate dimensions for the device, one embodiment of an above example has a main tube (102) approximately 60 mm in length where the interior diameter varies from approximately 12.5 to 18 mm along its length. Proceeding from the proximal end (106) of the main tube (102) along the length of the main tube (102), at approximately 17 mm from the proximal end (106) of the main tube (102), the interior wall (112) of the main tube (102) begins to narrow to form the deflecting wall (124). The inner diameter of the main tube (102) narrows steadily from approximately 18 mm to approximately 12.5 mm over the next 7.5 mm in tube length. The inner diameter of the main tube (102) then widens slightly from 12.5 mm to 13.1 mm in diameter over the next 6 mm in length. The inner diameter of the main tube (102) remains relatively constant over the next 11 mm in tube length and then widens abruptly to approximately 15.2 mm in inner diameter for the final 18 mm of tube length to accommodate a standard tube connecter. In this example, each of the supplementary respirable gas inlets (126) are substantially rectangular box-shaped, approximately 2 mm in length with the cross-section being a square approximately 0.5 mm by 0.5 mm, and cross-sectional area of approximately 0.25 square mm. The entry from the distribution ring (120) into the supplementary respirable gas inlets (126) and exit from the supplementary respirable gas inlets (126) into the main channel (102) are each angled at about 50 degrees (parallel to one another) relative to the inner surface (112) of the main tube outer shell (108) in accord with the angle at which the distribution ring/safety fin insert piece (110) abuts the main tube outer shell (108) in this region.

The above detailed measurements describe a non-limiting example and the device may of course be of any suitable length, diameter and configuration within the spirit of the invention.

Embodiment with Ball and Spring Pressure Relief Valve

Figure 4A:
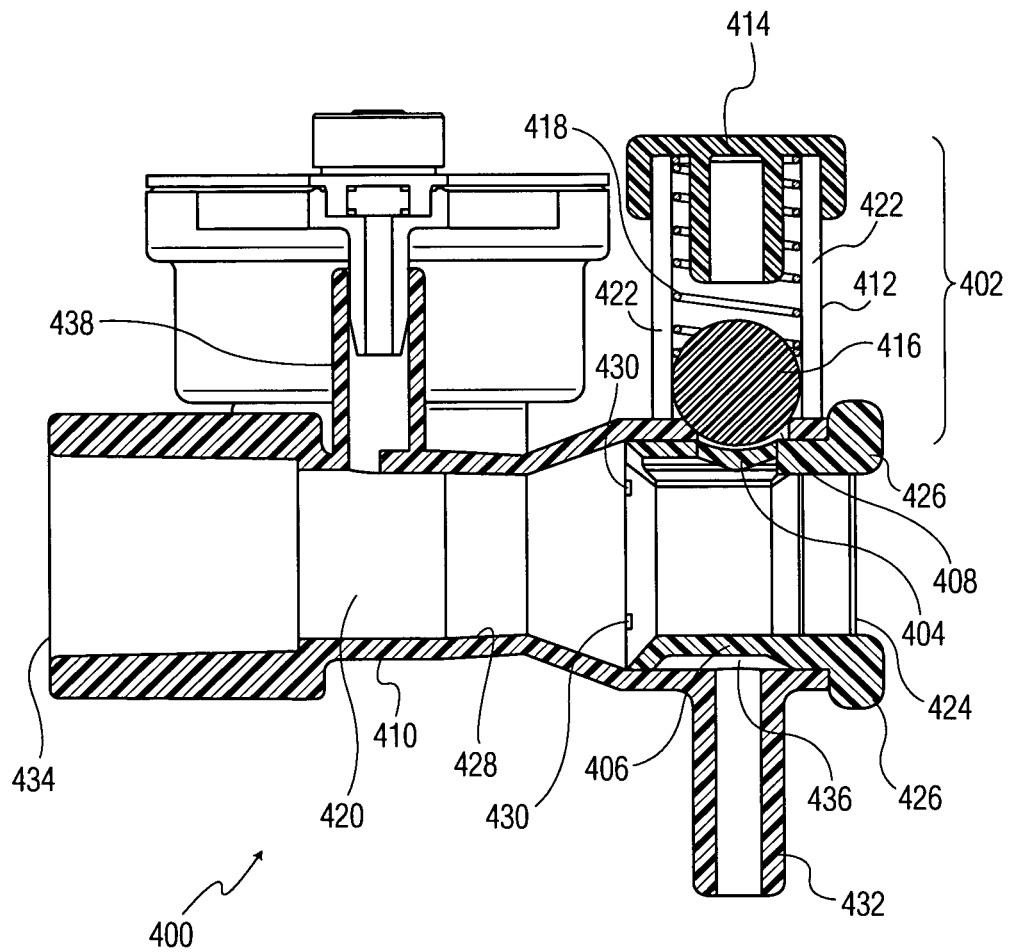
FIG. 4A shows a sectional view of an example of a breathing assistance device with a pop-off safety pressure relief valve according to the present invention.
Figure 4B:
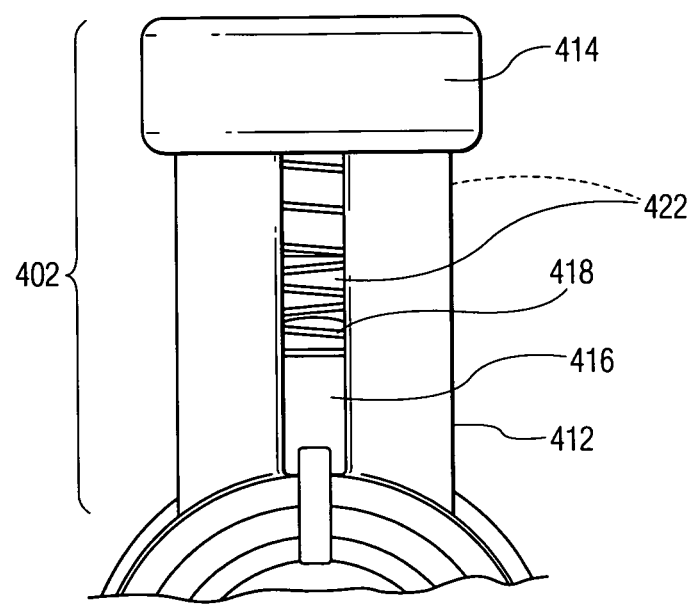
FIG. 4B shows the proximal end view of an example of a pop-off safety pressure relief valve.
Figure 5:
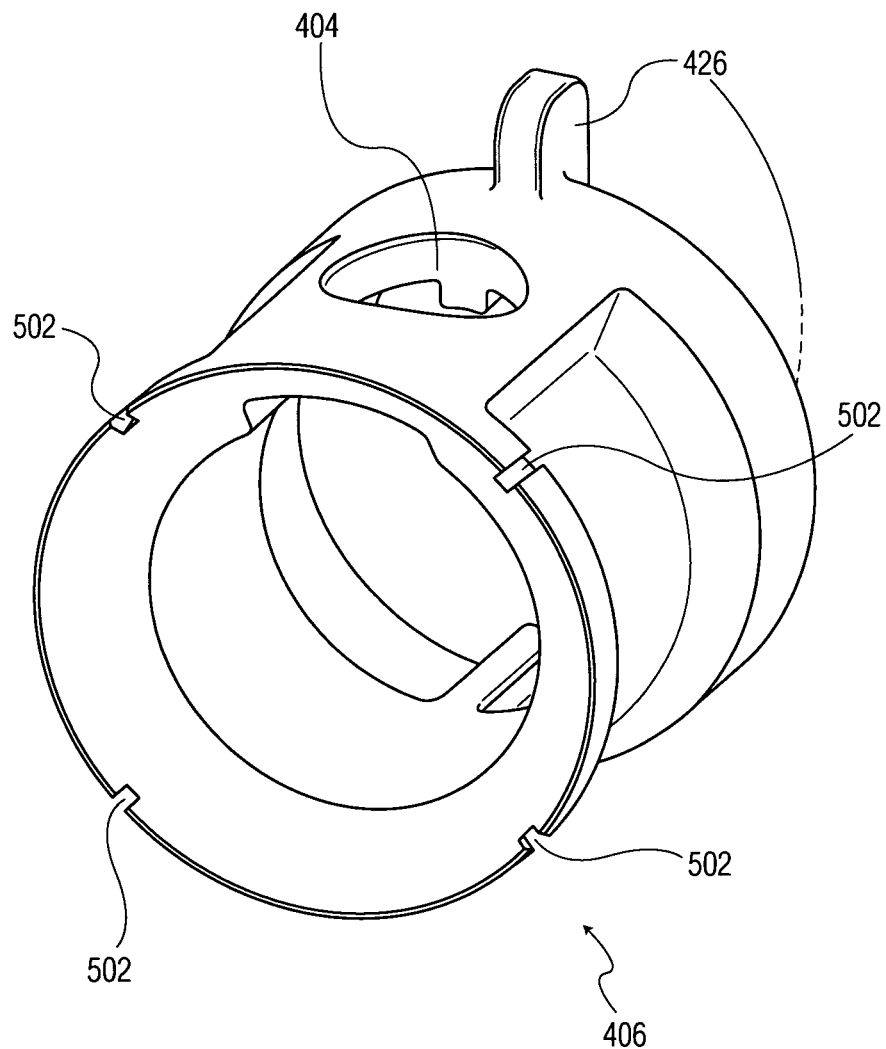
FIG. 5 shows an oblique angle view of an example of a distribution ring/safety fin insert piece for an embodiment of the present invention that includes a pop-off safety relief valve.

Referring to FIGS. 4A, 4B, and 5, a second illustrated example (400) of the invention further comprises a ball and spring "pop-off" safety relief valve (402). A pressure relief throughhole (404) made through the wall of the distribution ring/safety fin insert piece (406) is aligned with a pressure relief throughhole (408) made through the wall of the main tube outer shell (410). A "pop-off" safety relief valve housing (412) with pop-off housing endcap (414) encases the ball (416) and spring (418) mechanism and is attached to the main tube outer shell (410) covering the throughholes (404, 408) such that the spring (418) presses the ball (416) into the throughhole (408) through the main tube outer shell (410), blocking gas from escaping through the throughholes (404, 408). The spring (412) is calibrated such that it holds the ball (416) in position blocking the throughholes (404,408) until a threshold pressure is reached within the interior of the main tube (420). When the pressure within the main tube (420) rises to or above the threshold pressure, the spring (412) is compressed as the ball (416) is pushed away from the throughholes (404, 408) by the pressurized gas within the main tube (420), allowing gas to escape the interior of the main tube (420) and out through the 2 pressure release vents (422) in the side of the "pop-off" safety relief valve housing (412), thereby decreasing the excess pressure within the main tube (420). An example of an appropriate threshold pressure for CPAP application of a device constructed according to this example would be 25+/−5 cm $H_2O$, but an appropriate range might be anywhere from 15 to 45 cm $H_2O$ depending upon preference and application. Thus, a safety pressure relief is provided in the case of overpressure within the main tube (420) e.g. because the proximal end (424) of the main tube (420) is blocked by an obstruction, etc. This safety pressure relief valve (402) affords an added measure of safety to the patient in addition to that provided by the safety fins (426) of the distribution ring/safety fin insert piece (406).

The "ball and spring" mechanism (402) placed as described above is a non-limiting example of a pressure relief mechanism. Other types of safety pressure relief mechanisms known in the art may be used, such as for example, a safety sleeve as described in U.S. Pat. No. 5,036,847. Even an open hole might be utilized to afford additional protection from overpressure to the patient. There are, of course, numerous other possibilities that could be employed within the scope of the invention. And any such pressure relief mechanism could likewise be placed in alternative locations along the length of the main tube (420) to provide an additional safety pressure relief in the event of overpressure within the main tube (420) of the device.

An example of appropriate dimensions for this second example of a breathing assistance device according to the present invention would be like those detailed in the first example above.

Specialized Inlet Design for Improved Supplementary Respirable Gas Flow

In the examples illustrated in FIGS. 1 to 5, the supplementary respirable gas inlets (126, 430) are substantially in the shape of a rectangular box with angled rectangular openings. However, experimentation has shown that improved pressure characteristics at the distal (patient) end of the device may be achieved by altering the shape of these inlets.

Figure 6A:
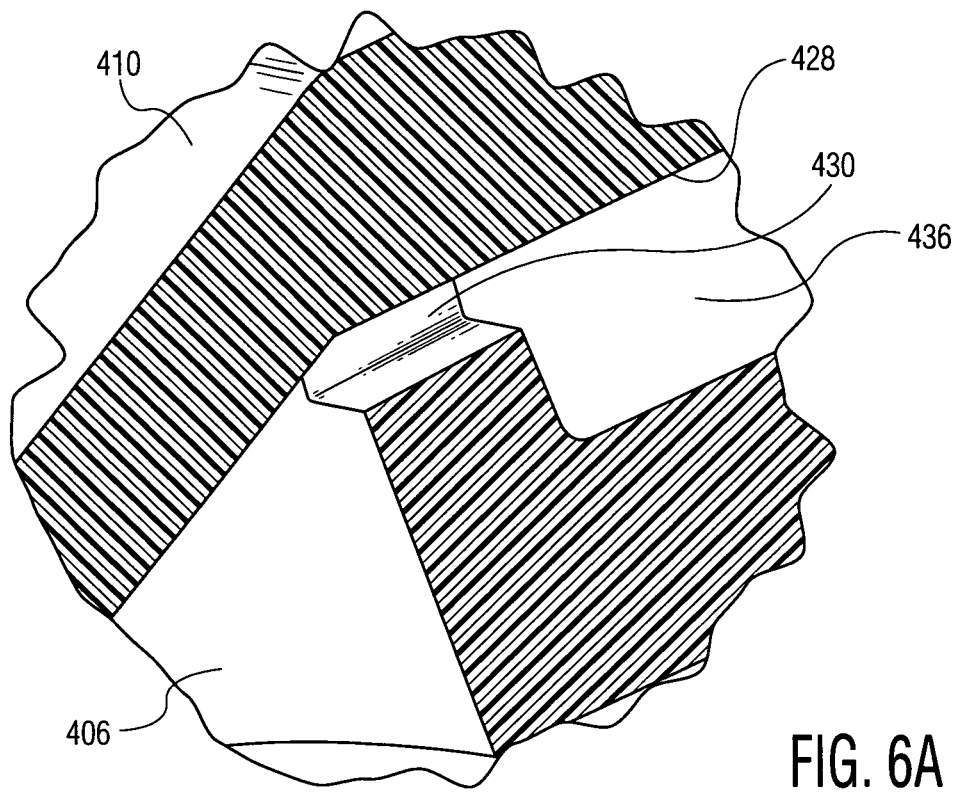
FIG. 6 shows a comparison between the rectangular box-shaped supplementary respirable gas inlet (6A) and a specialized supplementary respirable gas inlet (6B).

First, a prototype device (400) with measurements according to those given in the first example above and with pop-off safety relief valve according to the second example above was constructed and tested. Referring to FIG. 6a, a supplementary respirable gas inlet (430) of this prototype can be seen in greater detail. This prototype comprises 4 substantially rectangular-box-shaped supplementary respirable gas inlets (430) each with (parallel) entry and exit openings angled at 50 degrees relative to the interior surface of the main tube outer shell (428), and each inlet having a length of approximately 2.0 mm and substantially square cross-section of approximately mm 0.5 mm×0.5 mm. The two lengthwise edges of the supplementary respirable gas inlets (430) provided by the molding of the distribution ring outlet notches (502) of the distribution ring/safety fin insert piece (406) are rounded. The two lengthwise edges of the supplementary respirable gas inlets (430) formed where the distribution ring/safety fin insert piece (406) abuts the interior surface (428) of the main tube outer shell (410) are substantially right angles. When 25 standard liters/minute of supplementary respirable gas was insufflated into the side port (432) of the device, the result was a steady pressure of 7.1 to 7.4 cm of $H_2O$ at the distal end opening (434) of the device (400).

Figure 6B:
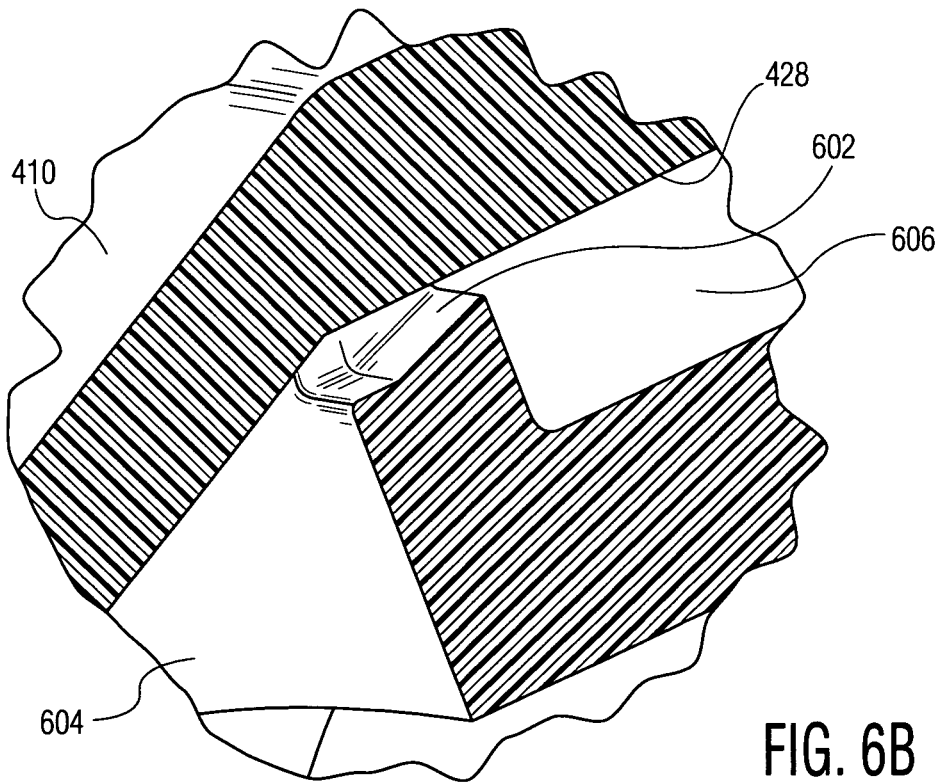
Figure 7:
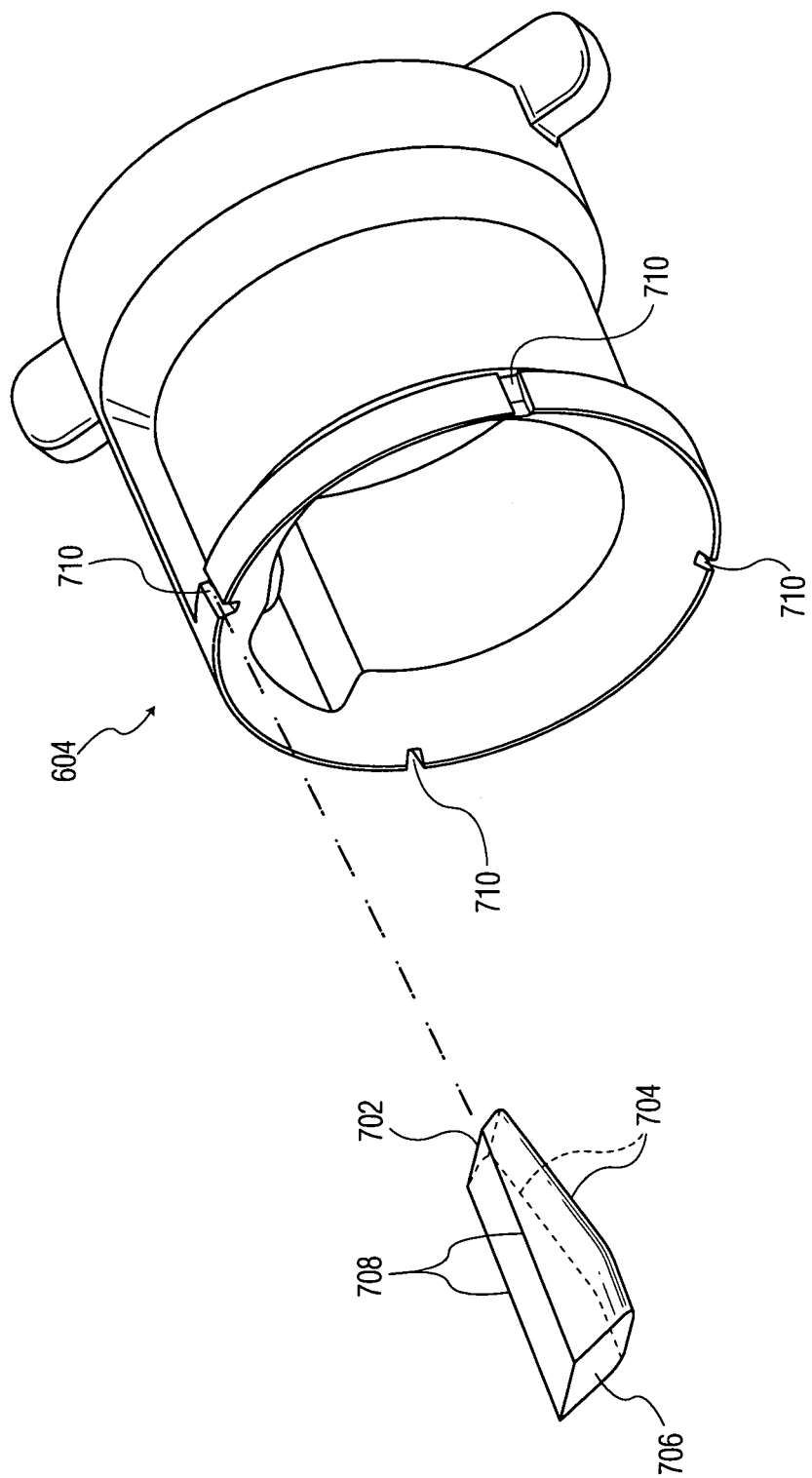
FIG. 7 shows an oblique angle view of an example of a specialized respirable gas inlet and its orientation relative to an oblique angle view of an example of a distribution ring/safety fin insert piece for an embodiment of the present invention that includes specialized respirable gas inlets.

Next, the same test was performed on a device having identical dimensions to the prototype device tested above except that the supplementary respirable gas inlets (602) are shaped differently. Referring to FIGS. 6b and 7, a specialized supplementary respirable gas inlet (602) of this prototype can be seen in detail. The specialized supplementary respirable gas inlets (602) are formed at the juncture between an alternately designed safety fin/distribution ring insert piece (604) and the interior wall (428) of a main tube outer shell (410) as in the previous example. The specialized supplementary respirable gas inlets (602) of this example are also 0.5 mm in width along their length. At their largest point, these specialized supplementary respirable gas inlets (602) have a substantially square cross-section with 2 rounded corners and with dimensions of approximately 0.5 mm×0.5 mm, similar to the previously tested rectangular-box-shaped respirable gas inlets (430). And the specialized supplementary respirable gas inlets (602) are also approximately 2 mm in total length, similar to the previously tested rectangular-box-shaped supplementary respirable gas inlets (430).

However, the specialized supplementary respirable gas inlets (602) differ from the previously tested rectangular-box-shaped supplementary respirable gas inlets (430) in that each specialized supplementary respirable gas inlet (602) is tapered along a portion of its length. Starting from the distribution ring opening (702), each specialized supplementary respirable gas inlet (602) measures 0.20 mm in height, as measured perpendicular from the interior surface (428) of the main tube outer shell (410), by 0.5 mm in width. Moving toward the interior of the main tube (420) along the length of the specialized supplementary respirable gas inlet (602), the dimensions of the cross-section steadily expand to 0.5 mm in height×0.5 mm in width along the first 1.0 mm in length of the specialized supplementary respirable gas inlet (602) (as measured along the interior surface (428) of the main tube outer shell (410)). The specialized supplementary respirable gas inlet (602) then continues at 0.5 mm in height×0.5 mm in width for the rest of its length towards the opening into main channel (706). Taking into account the angled distribution ring opening (702), the smallest cross-sectional area along the flow path through the specialized supplementary respirable gas inlet (602) is approximately 0.14 to 0.15 square mm.

As in the previous prototype, the two lengthwise edges (704) of the specialized supplementary respirable gas inlet (602) which are provided by the distribution ring/safety fin insert piece (604) are rounded as opposed to being right angle corners. And likewise, the two lengthwise edges of the specialized supplementary respirable gas inlet, created where the distribution ring/safety fin insert piece (604) abuts the interior wall (428) of the main tube outer shell (410), are substantially right angle edges. And also as in the previous prototype, the entry opening (702) from the distribution ring into each specialized supplementary respirable gas inlet (602) and exit opening (706) from each specialized supplementary respirable gas inlet (602) into the main channel (420) are parallel to one another and each angled at about 50 degrees relative to the interior surface (428) of the main tube outer shell (410), in accord with the angle at which the distribution ring/safety fin insert piece (604) abuts the main tube outer shell (410) in this region.

Together, the architecture of the distribution ring (606) in conjunction with the specialized supplementary respirable gas inlets (602) provide gas flow passages which initially converge more at the openings (702) from the distribution ring (606) into the specialized supplementary respirable gas inlets (602) than the analogous gas flow passages in the prototype which utilizes the substantially rectangular box-shaped supplementary respirable gas inlets (430). The gas flow passages through the device comprising the specialized supplementary respirable gas inlets (602) then diverge in the widening portion of each specialized supplementary respirable gas inlet (602). Thus these gas flow passages each converge and then diverge prior to opening into the interior of the main tube (420) in this example. In the prototype which utilizes the substantially rectangular box-shaped inlets (430), there is comparatively less convergence at the entries into the inlets (430) from the distribution ring (436), as the rectangular box shaped inlet (430) openings are larger, and there is also no subsequent divergence of the inlets (430) before opening into the main channel (420).

Testing of a device comprising 4 specialized supplementary respirable gas inlets (602) showed increased pressure at the distal end (patient end) (434) of the device as compared to the previously tested example using the rectangular box-shaped inlets (430). At 25 standard liters/minute of supplementary respirable gas flow into the side port (432) of the device utilizing the specialized supplementary respirable gas inlets (602), the result was a steady pressure of 9.2 to 9.6 cm of $H_2O$ a the distal end of the device (434). Thus for the same flow rate of supplementary respirable gas input into the device via the side port (432), there is approximately a 30% increase in resultant pressure at the distal end (434) of the device utilizing the specialized supplementary respirable gas inlets (602) when compared to the device which utilizes a rectangular-box-shaped inlet (430).

This increase in pressure means that a greater pressure can be achieved at the patient end (434) of the device with the same amount of supplementary respirable gas flow into the device from the supplementary respirable gas source or that the same pressure can be achieved using less gas from the supplementary respirable gas source. This is particularly advantageous when applying CPAP in situations where a limited supplementary respirable gas supply is available; for example where portable containers are used on site in emergency situations. The greater efficiency allows a limited supplementary respirable gas supply to still provide necessary CPAP pressure but to last longer.

Applicant believes that the reason why a superior performance is achieved in the prototype comprising the specialized supplementary respirable gas inlets (602) is due to the greater initial convergence of the gas flow passages leading into the specialized supplementary respirable gas inlets (602) followed by a diverging section within each specialized supplementary respirable gas inlet (602). It is believed that the velocity of the supplementary respirable gas increases as it passes through these passages. It is also possible that turbulence is reduced in these pathways as compared to the flow through the rectangular box shaped inlets (430). The result of this design modification is however clearly that there is an advantageous increased gas pressure at the distal end of the device comprising the specialized supplementary respirable gas inlets (602) when compared to the prototype that comprises the substantially rectangular box-shaped inlets (430) at the same insufflated gas flow rate.

The examples given above are meant to be non-limiting examples of ways to practice the current invention. Many varied embodiments may be conceived which fall within the scope and spirit of the present invention.

Although the above examples illustrate a main tube (102, 420) with distal end (104, 434) designed to be engaged with a standard connector (for attachment to a mask, an endotracheal tube, etc.), alternatively, the distal end (104, 434) of the main tube (102, 420) may be molded to any desired shape and size for the purpose of engaging with the breathing tract of the patient. For example, the distal end (102, 420) may be molded into a mask, a mouthpiece, an endotracheal tube, etc.

In the above examples, the 2 component pieces which comprise the main tube (102, 420), the main tube outer shell (108, 410) and the distribution ring/safety fin insert piece (110,406, 604), are both made from molded polycarbonate plastic. However, plastic formed in this manner is a non-limiting example of a suitable material and the device may be fashioned from any suitable materials, for example styrene, acetal, polypropylene, etc.

In the above examples, the main conduit is a substantially straight tube (102, 420) but the invention may be practiced with a main conduit of any suitable shape. The main conduit may, for example, include reservoir areas, bends, curves, etc. as desired while still remaining within the scope of the present invention.

In the above examples, the illustrated distribution ring (120, 436, 606) with 4 supplementary respirable gas inlets (126, 430, 602), comprising the described distribution ring outlet notches (306, 502, 710), illustrate limited examples of suitable supplementary respirable gas inlet configurations. Other suitable configurations rather than the illustrated distribution ring/supplementary respirable gas inlet configurations, utilizing, for example, more or less supplementary respirable gas inlets (126, 430, 602), longer molded channels or additional tubes with or without a distribution ring (120, 436, 606), etc., could likewise be employed to produce the desired function of injecting supplementary respirable gas into the interior of the main channel (102, 420).

In the above examples, a deflection means is created by the narrowing of the interior wall (112, 428) of the main tube (102, 420) beginning just distal of the supplementary respirable gas inlets (120, 436, 606). This is one non-limiting example of a deflection means configuration and other suitable deflection wall configurations or deflection means configurations could be utilized in order to successfully practice the invention. For example, individual deflection walls could be placed distal to each supplementary respirable gas inlet (126, 430) opening rather than using a single wall around the entire circumference of the interior wall (112, 428) of the main tube, etc.

In the above examples, the side ports (116, 432) and manometer ports (118, 438) are integrally molded features of the main tube outer shell (108, 410) but they could likewise be separate pieces attached to the main tube outer shell, etc.

In the above examples, the manometer port (118, 438) is located approximately one third of the way along the length of the main tube (102, 420) from the distal end (104, 434) of the device. This is a non-limiting example of the placement of the manometer port. A disposable manometer and a pressure tap could be placed in any suitable desired location along the length of the tube.

The specialized supplementary respirable gas inlet (602) was only described and tested in conjunction with the device which included a pop-off safety pressure relief valve (402). Among multiple possible configurations within the scope of the invention, these specialized supplementary respirable gas inlets (602) could likewise be incorporated into an embodiment of the invention which does not include a pop-off safety pressure relief valve.

In the above examples the proximal end (106, 424) of the device is left open to the atmosphere. However, the proximal end (106, 424) need not be left wide open in order for the interior of the main conduit (102, 420) to be in fluid communication with the atmosphere. For example, a filter could be placed within, over, or within an extension of the proximal end (106, 424) while still retaining the desired characteristic of fluid communication of the interior of the main conduit (102, 420) with the atmosphere, allowing for exhalation out the proximal end (106, 424), release of excess pressure, as well as influx of fresh atmospheric air into the device. Likewise, other devices that allow fluid communication of the interior of the main conduit (102, 420) with the atmosphere through the proximal end (106, 424) could be placed within, over, or as extensions of the proximal end (106, 424) while still allowing the desired function.

In addition to these suggestions, other suitable variations within the spirit of the invention could likewise be made and still remain within the scope of the claimed invention.

We claim:

1. A disposable breathing assistance device comprising:
a conduit having a distal end and a proximal end and a main channel extending therebetween, said distal end of said conduit either adapted to be engaged directly with a patient's breathing tract or adapted to be engaged indirectly with a patient's breathing tract, said proximal end of said conduit in fluid communication with the ambient atmosphere;
a side port, said side port adapted to be supplied with supplementary respirable gas by a respirable gas source and for injecting supplementary respirable gas into an interior of said conduit;
a manometer affixed to the conduit and in fluid communication with the interior of said conduit;
a supplementary respirable gas distribution ring adapted to be supplied with the supplementary respirable gas from the side port, the distribution ring adapted to supply the supplementary respirable gas to one or more of supplementary respirable gas inlets, the one or more of supplementary respirable gas inlets delivering the supplementary respirable gas into the main channel;
wherein each of the one or more of supplementary respirable gas inlets has a substantially rectangular cross section and the cross-sectional height of each of the one or more of supplementary respirable gas inlets has a first height at an end of the of the supplementary respirable gas inlets closest to the side port and a height of each of the one or more of supplementary respirable gas inlets linearly increases towards the main channel.

2. The device of claim 1 where said main channel is substantially linear.

3. The device of claim 1 where said main channel is substantially tubular.

4. The device of claim 1 further comprising means for deflecting a flow of said supplementary respirable gas from the one or more of supplementary respirable gas inlets towards a cross-sectional center of the main channel.

5. The device of claim 4 where the means for deflecting comprises one or more deflection walls.

6. The device of claim 1 where a supplementary respirable gas flow passage fluidly connects the supplementary respirable gas distribution ring to the main channel, the supplementary respirable gas flow passage having a reduced cross-sectional area with respect to a central cross-sectional area prior to opening into the interior of the conduit.

7. The device of claim 1 further comprising a safety pressure relief located along a length of said main channel for releasing excess pressure from the interior of said conduit.

8. The device of claim 7 where said safety pressure relief is a ball and spring pop-off safety valve calibrated to release excess pressure from the interior of said conduit if the pressure within said conduit exceeds a predetermined level.

9. The device of claim 7 where said safety pressure relief is located between the proximal end of the conduit and the length along the main channel where said one or more of supplementary respirable gas inlets opens into the interior of said conduit.

10. The device of claim 1 where said main channel is substantially linear, said main channel further comprising a deflection wall, the deflection wall directing a flow of said supplementary respirable gas from the one or more of supplementary respirable gas inlets towards a cross-sectional center of the interior of said conduit.

11. A disposable CPAP device comprising:
a conduit having a distal end and a proximal end and a main channel extending therebetween, said distal end of said conduit adapted to be engaged either directly or indirectly with a patient's breathing tract, said proximal end of said conduit in fluid communication with the ambient atmosphere;
a side port, said side port adapted to be supplied with a supplementary respirable gas for injecting the supplementary respirable gas into an interior of said conduit; and
a supplementary respirable gas distribution ring adapted to be supplied with supplementary respirable gas from the side port, the supplementary respirable gas distribution ring having one or more of supplementary respirable gas inlets, the supplementary respirable gas flows from the side port, through the one or more of supplementary respirable gas inlets and into the main channel, each of the one or more of supplementary respirable gas inlets has a substantially rectangular cross section and the cross-sectional area of each of the one or more of supplementary respirable gas inlets has a first area at an end of the one or more of supplementary respirable gas inlets closest to the side port and a second area at a point distal from the side port, wherein the second area is greater than the first area;
a manometer affixed to the conduit and in fluid communication with the interior of said conduit for determining a gas pressure within said main channel.

12. The device of claim 11 where said main channel is substantially linear.

13. The device of claim 11 where the cross-sectional area of each of the one or more of supplementary respirable gas inlets further has a third cross-sectional area at a distal end of the of the one or more of supplementary respirable gas inlets farthest from the side port, wherein the second cross-sectional area is less than the third cross-sectional area.

14. The device of claim 11 further comprising a deflection means to deflect the flow of said supplementary respirable gas from the one or more of supplementary respirable gas inlets towards the cross-sectional center of the interior of said conduit.

15. A disposable breathing assistance device comprising:
a conduit having a distal end and a proximal end and a main channel extending therebetween, said distal end of said conduit either adapted to be engaged directly or indirectly with a patient's breathing tract, said main channel of said conduit in fluid communication with the ambient atmosphere through said proximal end;
at least one supplementary respirable gas inlet injecting a supplementary respirable gas into said main channel, said at least one supplementary respirable gas inlet adapted to be supplied with supplementary respirable gas from a respirable gas source;
each of the at least one supplementary respirable gas inlet having a substantially rectangular cross section and the cross-sectional height of each of the at least one supplementary respirable gas inlet having a first height at an end of the of the at least one supplementary respirable gas inlet closest to the respirable gas source and a second height at a point closest to the main channel, wherein the second height is greater than the first height; and
a manometer affixed to the conduit and in fluid communication with an interior of said conduit.

* * * * *